United States Patent [19]
Young et al.

[11] Patent Number: 6,136,405
[45] Date of Patent: Oct. 24, 2000

[54] SHEET MATERIAL HAVING A FIBROUS SURFACE AND METHOD OF MAKING THE SAME

[75] Inventors: Terrill Alan Young; George Christopher Dobrin; Dennis Albert Thomas, all of Cincinnati, Ohio

[73] Assignee: The Procter & Gamble Company, Cincinnati, Ohio

[21] Appl. No.: 08/683,944

[22] Filed: Jul. 19, 1996

Related U.S. Application Data

[63] Continuation of application No. 08/514,474, Aug. 11, 1995, Pat. No. 5,565,255, which is a continuation of application No. 08/298,109, Aug. 29, 1994, abandoned.

[51] Int. Cl.⁷ .............................. A61F 13/66; B32B 3/06; B32B 33/00
[52] U.S. Cl. ........................... 428/92; 428/100; 604/391
[58] Field of Search ..................... 428/92, 100; 604/391

[56] References Cited

U.S. PATENT DOCUMENTS

| | | |
|---|---|---|
| 4,077,410 | 3/1978 | Butterworth .......................... 128/287 |
| 4,081,301 | 3/1978 | Buell ...................................... 156/164 |
| 4,463,045 | 7/1984 | Ahr et al. .............................. 428/131 |
| 4,610,673 | 9/1986 | Weisman et al. .................... 604/368 |
| 4,652,484 | 3/1987 | Shiba et al. .......................... 428/286 |
| 4,828,556 | 5/1989 | Braun et al. .......................... 604/365 |
| 4,863,779 | 9/1989 | Daponte ................................ 428/152 |
| 4,919,738 | 4/1990 | Ball et al. ............................. 156/73.5 |
| 4,941,939 | 7/1990 | Nomura et al. ...................... 156/495 |
| 5,058,247 | 10/1991 | Thomas et al. ........................ 24/448 |
| 5,069,677 | 12/1991 | Sakurai et al. ....................... 604/370 |
| 5,116,563 | 5/1992 | Thomas et al. ...................... 264/167 |
| 5,180,534 | 1/1993 | Thomas et al. ...................... 264/145 |
| 5,565,255 | 10/1996 | Young et al. ........................... 428/92 |
| 5,618,583 | 4/1997 | Young .................................... 427/277 |

*Primary Examiner*—James C. Cannon
*Attorney, Agent, or Firm*—Larry L. Huston; J. Daniel Lykins

[57] ABSTRACT

A process for forming a sheet material having a fibrous surface and the sheet material produced thereby; the fibers are produced by deposition of a heated, thermally sensitive material on to a substrate, which is transported at a velocity approximately equal to the velocity of the material being deposited, by manipulating the fiber density and denier, the sheet material can be made to be either softer or rougher to the touch.

11 Claims, 5 Drawing Sheets

SHEET MATERIAL HAVING A FIBROUS SURFACE AND METHOD OF MAKING THE SAME

This is a continuation of application Ser. No. 08/514,474, filed Aug. 11, 1995, now U.S. Pat. No. 5,565,255, which is a continuation of application Ser. No. 08/298,109, filed Aug. 29, 1994, and now abandoned.

FIELD OF THE INVENTION

The present invention relates to a sheet material having a fibrous surface and to a method for producing the same.

BACKGROUND OF THE INVENTION

Disposable, absorbent garments such as diapers and adult incontinence products typically have a three-layer construction. The first layer, which is the layer closest to the body of the wearer is a liquid permeable layer. The second layer, located between the first and third layers, acts to absorb the liquids which flow through the first layer. Finally, the third or outer layer is liquid impervious to keep the liquids from exiting the garment.

Typically the outer layer or backsheet is comprised of a thin, thermoplastic film, such as polyethylene. While the backsheet performs the function of not allowing liquids to exit a diaper, it lacks the aesthetic appeal of cloth. This cloth-like appearance especially appeals to older children and wearers of adult incontinence products. Adults who wear these products do not wish to be perceived as wearing a plastic looking "diaper." This rationale also applies to children as they become older. These children also do not want to be perceived as a "baby" wearing a "diaper." Furthermore, parents of children who wear diapers have consistently requested products which are aesthetically neat and attractive.

Previously, when a clothlike appearance was desired, it was known in the art to make a sheet material in a lamination process. U.S. Pat. No. 4,828,556 to Braun et al. discloses a breathable, multi-layered, cloth-like barrier to be used as an outer cover for a disposable, absorbent garment. Braun teaches a breathable, i.e., one which is pervious to water vapor, outer cover comprising a porous, meltblown, nonwoven web; a second layer, which is a continuous film of polyvinyl alcohol, and a third layer which comprises a porous, nonwoven web. The third layer is formed by spin bonding, melt bonding or laminating a spin bond to a melt bond, or vice versa. This third layer is a thermoplastic polymer and preferably a polyolefin, with polypropylene and polyethylene being most preferred.

This present invention is directed to a sheet material having a fibrous surface and a method for producing that sheet material. The sheet material is manufactured by depositing a thermally sensitive material onto a substrate and can be used in situations in which a cloth-like appearance and feel are required or desired for a particular garment. This invention also provides a means for manufacturing a sheet material having a fibrous surface which may be used to form disposable, absorbent garments. Thus, a sheet is provided for disposable diapers and adult incontinence products which offers the wearer the look and feel of a cloth diaper or incontinence product.

SUMMARY OF THE INVENTION

The sheet material of the present invention has a fibrous surface and includes a substrate having a plurality of essentially straight fibers bonded thereto and projecting outwardly from the substrate. Fiber, as referred to throughout the description of the invention and in the claims, is defined as that portion of the structure starting at the point where the change in diameter/change in length is less than 0.3 and continues until termination of the structure.

The process of the present invention involves a screen roll process which produces an array of flexible fibers having a distinctly cloth-like feel. The sheet material of the invention may be manufactured according to a process comprising the steps of heating a thermally sensitive material sufficiently to reduce its viscosity for processing, and preferably to at least its melting point, depositing the thermally sensitive material onto the substrate in discrete amounts, drawing the deposited material outwardly from the substrate to form a fiber, and terminating the fiber.

A similar process has been used to manufacture a mechanical fastening hook, as disclosed in commonly assigned U.S. Pat. No. 4,058,247 to Thomas et al. The patent discloses a modified Gravure printing process used to deposit discrete amounts of thermally sensitive material onto a substrate to create the hooks. The hooks are printed on the substrate at a density of approximately 81 hooks per square centimeter. The thermally sensitive materials employed in the '247 patent, polyamide and polyester hot melt adhesives, produce rigid arrays of hooks having a distinctly uncloth-like feel.

BRIEF DESCRIPTION OF THE DRAWINGS

While the specification concludes with claims particularly pointing out and distinctly claiming the present invention, it is believed that the invention is better understood from the following description taken in conjunction with the associated drawings, in which like elements are designated by the same reference numeral and:

DETAILED DESCRIPTION OF THE INVENTION

Figure 4:
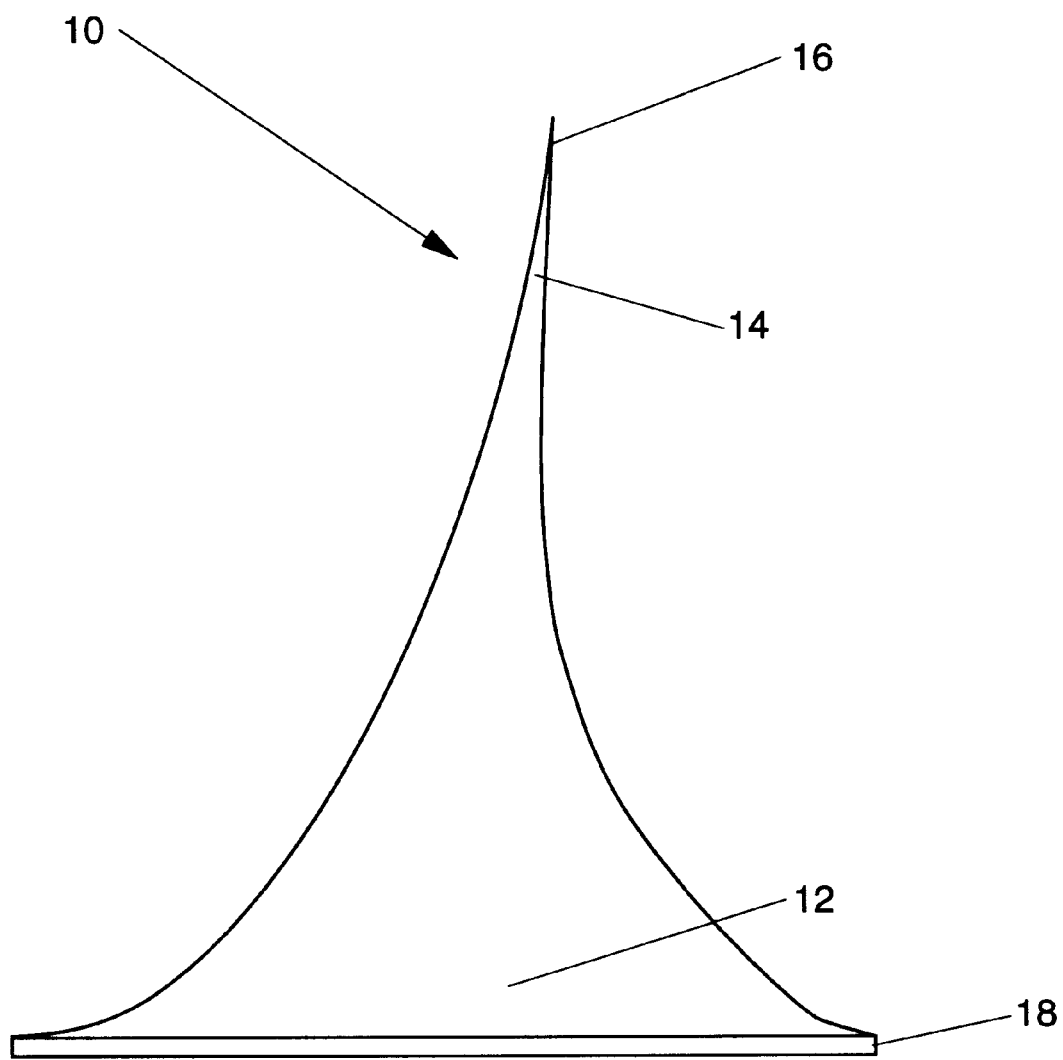
FIG. 4 is a schematic profile view of a fiber produced according to the present invention.

The sheet of material of the present invention comprises a substrate 18 having a plurality of flexible fibers 10, bonded to at least one surface of the substrate 18. Each fiber 10 of the sheet may be joined to a substrate 18 in a predetermined pattern. Each of the fibers has a base 12 and a shank 14 as illustrated in FIG. 4. The bases 12 of the fibers 10 contact and are joined to the substrate 18 and support the fiber shanks 14 which project outwardly from the substrate 18 and bases 12. The shanks 14 terminate at the distal end 16 of the fiber 10.

Figure 5:
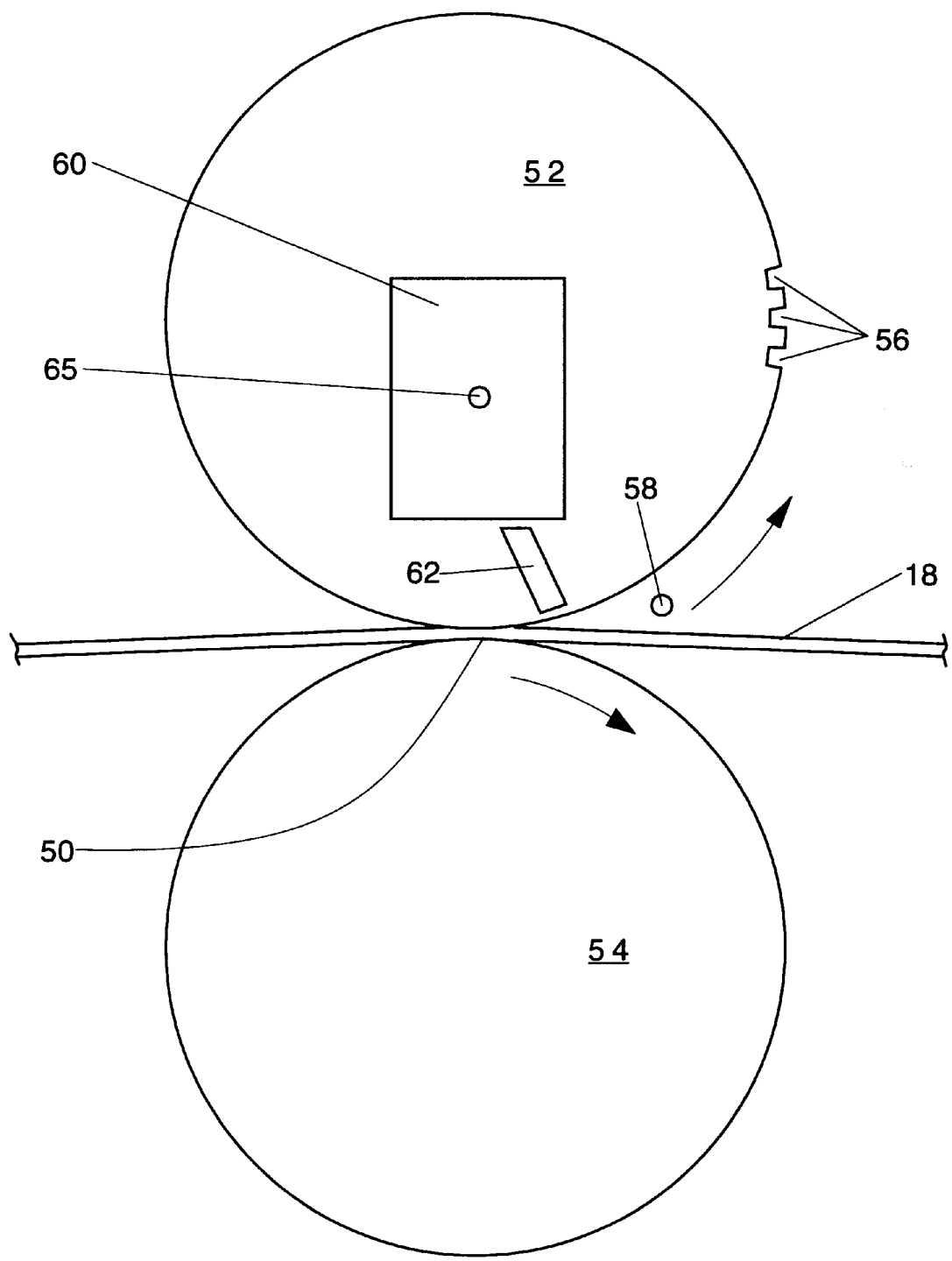
FIG. 5 is a side elevational view of one apparatus which can be used to produce a cloth-like sheet of the present invention.

An array of fibers 10 may be provided on the surface of a paper or film by any suitable apparatus and method, including methods which yield a free formed fiber 10 as described and claimed herein below. As used herein, the term "free formed" means a structure which is not removed from a mold cavity or extrusion dye in solid form or with a defined shape. The fibers 10 are deposited onto a substrate in a molten, preferably liquid state, and solidify by cooling, preferably freezing, until rigid, into the desired structure and shape as described hereinafter. The free formed fiber 10 or array of fibers 10 may be produced by manufacturing processes which are similar to those processes commonly known as gravure printing and screen printing. Using the screen printing process, a generally planar substrate 18 having opposed faces is passed between the nip 50 of two generally cylindrical rolls, a screen roll 52 and a backing roll 54, as illustrated in FIG. 5. The rolls 52 and 54 have generally parallel centerlines and are maintained in contacting relationship with the substrate 18 as it passes through the nip 50. The first roll 52, referred to as the screen roll, has a screen 56 which has the desired pattern for the fibers to be deposited on the substrate. The second roll 54, referred to as the backing roll, provides support and reaction against the screen roll 52 to position the substrate 18 against the screen roll 52 as the substrate 18 passes through the nip 50.

Thermally sensitive materials, preferably thermoplastic material, from which the fibers 10 are to be formed is supplied from a heated source, such as a trough (not shown). The thermally sensitive material is heated, preferably to at least its melting point, and is introduced onto the screen 56 as the screen roll 52 is rotated about its centerline. A doctor blade 62 forces the thermally sensitive material through the screen 56 onto the substrate 18 in the desired pattern.

As relative movement between the substrate 18 and rolls 52 and 54 continues, the fibers 10 are stretched or drawn in a direction having a vertical component, imparting a length to the fiber 10. When the fiber 10 reaches a desired length, the fiber 10 may be severed by a severing means 58 or the fiber 10 may be stretched until breakage without the use of a dedicated severing means. The fiber 10 then cools, and preferably freezes, into a solid structure.

Upon solidification of the fiber material, if desired, the fibers 10 may then be formed into a nonwoven matrix. For example, the fibers may be bonded together to the substrate by using pressure rolls or other methods commonly used in the industry to form nonwoven matrices. As used herein, the term "nonwoven" means that the fibers 10 are not systematically woven. The fibers 10 instead are formed into a random network.

The substrate 18 of the sheet material should be strong enough to preclude tearing or separating between the individual fibers 10, to provide a surface to which the fibers 10 will readily adhere, and preferably to be capable of being joined to or formed into an article of clothing. The substrate 18 should also be capable of being rolled to support conventional manufacturing processes, be flexible so it may be bent and flexed in a desired configuration, and be able to withstand the heat of the thermoplastic material being deposited thereon without melting or incurring deleterious effects until the fibers solidify. The substrate 18 should also be available in a variety of widths.

Suitable substrates 18 include knitted fabrics, woven materials, non-woven materials, rubber, vinyl, particularly polyolefinic films, and paper. Preferably, the polyolefinic film is a polyethylenic film having a thickness of 0.5 to 1.5 mils. A suitable polyethylene film is manufactured by Tredegar Film Products and marketed in the trade as P8570. Furthermore, any of the backing films previously used to manufacture disposable, absorbent garments would be suitable for use as substrate, including porous film sheets. A suitable porous polyethylene film is manufactured by Tredegar Film Products and sold in the trade as P5652.

The base 12 of the fiber 10 is the generally planar portion of the fiber 10 which is attached to the substrate 18 and is contiguous with the proximal end of the shank 14 of the fiber 10. As used herein, the term "base" refers to that portion of the fiber 10 which is in direct contact with the substrate 18 and supports the shank 14 of the fiber 10. It is not necessary that a demarcation be apparent between the base 12 and the shank 14 of the fiber 10. It is only important that the shank 14 not separate from the base 12 and that the base 12 not separate from the substrate 18 during use.

The shape of the footprint of the base 12 on the substrate 18 is not critical and may be amplified in any direction to provide greater structural integrity. As used herein, the term "footprint" refers to the planar contact area of the base on the substrate 18. The aspect ratio (length to width ratio) of the sides of the footprint should not be too great, otherwise the fiber 10 may be unstable when subjected to forces parallel to the shorter side of the footprint. An aspect ratio of less than about 1.5:1 is preferred and a generally circular footprint is more preferred. For the embodiment described herein, a base 12 having a footprint of generally circular shape and approximately 0.02 mm to about 0.32 mm (0.002 to 0.0125 inches) in diameter is suitable.

The fibers 10 of this invention range in length from about 0.15 to about 65 mm long. Preferably, their lengths will be about 0.15 to about 0.5 mm.

The array of the fibers 10 may be provided in any pattern, pitch and density as desired. The pattern, pitch and density of the fibers 10 are primarily determined by the mesh of the screen 56 of the screen roll 52. The screen roll screen 56 has a mesh which ranges from about 50 to 200, and in the preferred embodiment, from about 100 to 200. Also, as the diameters of the base 12 and the fiber 10 decrease or the length of the fiber 10 increases, the cloth-like sheet becomes softer to the touch.

It is advantageous to dispose the array of fibers 10 in rows so that each fiber 10 is generally equally spaced from the adjacent fibers. Rows are generally oriented in the machine direction and cross-machine direction according to the manufacturing process described and claimed herein. Generally, each machine direction and cross-machine direction row of fibers 10 will be equally spaced from the adjacent machine direction and cross-machine direction rows of fibers 10, to provide a generally even feel to the touch. Of course, those skilled in the art will recognize that a variety of deposition patterns may be used. The fiber pitch may range from about 2.0 fibers per mm to about 8.0 fibers per mm and, in the preferred embodiment, about 6.1 fibers per mm.

The density of the fibers, number of fibers per unit of area, on the sheet material is primarily determined by the mesh size of the screen 56 of the screen roll 52. As the mesh size of the screen 56 increases, the density of the fibers on the sheet material correspondingly increases. Generally, as the mesh increases, the cloth-like sheet becomes softer to the touch because of the corresponding increase in density of the fibers. However, one skilled in the art will recognize that if the fibers 10 are too closely spaced, compacting and matting of the fibers 10 will occur. Conversely, if the fibers 10 are spaced too far apart, the sheet will take on a distinctly uncloth-like feel. The fibers of this invention will have a density of about 4 to about 62 fibers/mm$^2$ and preferably about 16 to about 49 fibers/mm$^2$. Most preferably, there will be about 37 fibers/mm$^2$.

Because of the cloth-like nature of this sheet, the fibers 10 can be measured in terms of denier. Denier, for the purposes of this invention, is defined as the weight, in grams, per 9,000 meters of fiber. The fibers of this invention have a denier which ranges from 0.20 to 6.0, and, in the preferred embodiment, from 0.5 to 1.5. The denier of a fiber, which results from the method of this invention, is calculated by measuring the diameter of the individual fiber, calculating the volume of a cylinder ($V=\Pi r^2 h$) and multiplying the volume by the density of the material, in grams/cm3, used to make the fibers.

The fibers 10 of this invention may be defined in terms of shear strength. They will have a shear strength of less than 50 grams/square meter, and preferably a shear strength of zero. A low shear strength is desirable because the wearer would not enjoy wearing an article which would interconnect with the wearer's clothing or body hair. Further, if the article were to have a high shear strength, the fibers would be more rigid and would not have a cloth-like feel.

As used herein, the term "shear strength" refers to force required to initiate a sliding of the fibers relative to the loop portion of a hook and loop fastener. To test the shear strength of these fibers, a sheet containing the fibers made by the method of this invention was placed upon a sheet containing the loop portion of a hook and loop fastener. The two sheets were then pulled in opposite parallel directions and the force required to initiate a movement between the two sheets was then measured as shear strength.

Shear strength may be measured according to the disclosure of commonly assigned U.S. Pat. No. 4,699,622, issued Oct. 13, 1987 to Toussant et al. The disclosure of this patent is incorporated herein by reference for the purpose of showing how to measure the shear strength of the present invention.

The fibers 10 of this invention may also be characterized in terms of peel strength. The fibers 10 of this invention have a negligible peel strength and preferably, a peel strength of about zero grams per square inch. As used herein, "peel strength" refers to the force required to move a sheet of fibers away from a sheet, containing the loop portion of a hook and loop fastener, in a direction perpendicular to the surface of the sheet containing the loops. Thus, the extremely low, almost non-existent, peel strength of the fibers 10 indicates the degree to which the fibers 10 would not engage with the wearer's clothing or body hair.

Peel strength may be measured according to ASTM Test Method D903-49 entitled "Peel or Stripping Strength of Adhesive Bonds." This test -method is incorporated herein by reference as a method of determining the peel strength of the present invention.

As contrasted with the fibers of the present invention, U.S. Pat. No. 5,180,534 to Thomas et al. discloses a fastening system employing a hook-like member composed of a thermoplastic material. The '534 patent discloses an embodiment in which the fastening system should resist a peel force of at least 200 grams and should resist a shear force of at lest 500 grams. The hooks described in the '534 patent would create a garment which would adhere to wearers clothes and body hairs, thus, creating a reasonably uncomfortable garment.

The thermally sensitive material should have a melting point low enough to provide for easy processing and relatively high viscosity to provide a tacky and tough consistency at temperatures near the material melting point, so that the fibers 10 may be stretched and formed according to the method of manufacture recited herein. As used herein, "thermally sensitive" refers to the property of a material which gradually changes from the solid state to the liquid state upon the application of heat. Typically, the melting point ranges from 85° C. to 150° C. It is also important that the fibers 10 be viscoelastic, to allow for more variation in the parameters affecting fiber structure. As used herein, the phrase "viscoelastic" describes the mechanical behavior of a material which exhibits viscous and delayed elastic response to stress in addition to instantaneous elasticity. Material having a complex viscosity ranging from about 50 to about 130 Pascal-seconds at the temperature of application to the substrate is suitable.

The fibers 10 are preferentially comprised of a thermoplastic material. The term "thermoplastic" refers to uncrosslinked polymers of a thermally sensitive material which flows under the application of heat or pressure. Hot melt adhesive thermoplastics are well-suited to manufacture the cloth-like fibers of the present invention, particularly in accordance with the process described and claimed below. As used herein, the phrase "hot melt adhesive" refers to a viscoelastic thermoplastic material which retains residual stresses upon solidification from the liquid state. Hot melt adhesives are particularly suitable and preferred, including ethylene vinyl acetate and polyethylene based adhesives. An adhesive having a complex viscosity of about 90±40 Pascal-seconds at about 100° C. has been found to work well. Some commercially available examples of useful hot melt adhesives include PRLMACOR® and EASTOBOND® A3 available from Dow Chemical and Eastman Chemical, respectively.

Process of Manufacture

The cloth-like sheet described above, may be manufactured according to the process comprising the steps of depositing discrete amounts of heated, thermally sensitive material onto a substrate which is transported relative to the selected means for depositing the heated, thermally sensitive material. More particularly, the process comprises the steps of providing a thermally sensitive material, as disclosed above, and heating it to at least the melting point so that the heated, thermally sensitive material is in a fluidic, flowable state.

A substrate 18 is provided and transported relative to the means for depositing 52 this heated material. A means for depositing 52 discrete amounts of the heated, thermally sensitive material is also provided. Discrete amounts of the heated, thermally sensitive material are deposited onto the substrate 18 from the depositing means 52. It will be apparent to one skilled in the art that the depositing means 52 for depositing discrete amount of thermally sensitive material may be transported and the substrate 18 held stationary or, preferably, the substrate 18 transported and the depositing means held stationary, to provide the relative motion between the substrate 18 and the depositing means 52.

The phrase "depositing means" refers to any apparatus which transfers liquid thermally sensitive material from a bulk quantity to the substrate in discrete amounts corresponding to individual fibers. The term "deposit" means to melt the thermally sensitive material from the bulk form and to dose such material onto the substrate in units corresponding to individual fibers.

During transport of the substrate 18 and the deposition of the discrete amounts of thermally sensitive material which form the fiber 10, two directions are defined. The first direction is the direction of the transport of the substrate 18 relative to the means for depositing 52 the thermally sensitive material. The second direction is the direction of deposition of such material onto the transported substrate 18 at the time of deposition. During the process for deposition of the heated, thermally sensitive material onto the substrate 18, a velocity differential may be incurred between the transported substrate 18 and the thermally sensitive material being deposited. Such a velocity differential is considered "positive," if the speed of the substrate 18 in the first direction is greater than the velocity of the depositing means at the point of deposition of such material onto the substrate. Conversely, a velocity differential is considered "negative" if the speed of the transported substrate is less than the velocity of the depositing means. It will be apparent to one skilled in the art that if the means for depositing the heated, thermally sensitive material is held stationary and the substrate is transported, a positive velocity differential results. The viscoelastic rheological properties of the thermally sensitive material may provide for lateral stretching of the material when a velocity differential exists. This lateral stretching will result in a fiber 10 having a degree of curl which is dependent upon the velocity differential. When no velocity differential exists, the thermally sensitive materials will experience only a horizontal stretching and no lateral stretching. Thus, a straight fiber 10 would result. This invention preferably employs no velocity differential between the transported substrate 18 and the thermally sensitive material being deposited so that an essentially straight fiber 10 results. As used herein, the phrase "essentially straight" means that the fiber does not include the hook portion of the refastenable mechanical fastening system as taught in commonly assigned U.S. Pat. No. 5,180,534 to Thomas et al. This definition, however, does not preclude the fiber from having a degree of curvature as found in other synthetic fibers. The fiber may be curved, for example, and not by way of limitation, to such an extent that the internal angles between any two points on the fiber and a straight line, which intersects the fiber at two points, are less than 70° and preferably less than 50°.

In operation, the substrate 18 is transported in a first direction relative to the depositing means 52. More particularly, the substrate 18 is transported through the nip 50, and preferentially drawn by a take-up roll (not shown). This provides a clean area of substrate 18 for continuous deposition of fibers 10 and removes the portions of the substrate 18 having fibers 10 deposited thereon. The direction generally parallel to the principal direction of transport of the substrate 18 as it passes through the nip 50 is referred to as the "machine direction." The machine direction is generally orthogonal to the respective centerlines of the screen roll 52 and backing roll 54. The direction generally orthogonal to the machine direction and parallel to the plane of the substrate is referred to as the "cross-machine direction." The "plane of the nip" is the plane having a line coincident with the nip 50 and tangent to both the screen roll 52 and the backing roll 54.

With continuing reference to FIG. 5, the cloth-like sheet according to the present invention may be manufactured using a screen roll printing process. The substrate 18 may be passed through the nip 50 formed between two juxtaposed rolls, a screen roll 52 and a backing roll 54. The rolls have substantially parallel mutual centerlines disposed generally parallel to the plane of the substrate 18. Each of the rolls 52 and 54 is rotated about its respective centerline so that the rolls have substantially the same surface direction, at the nip 50. Typically, the screen roll 52 will have a diameter of about 195 to 220 mm in laboratory practice but may range up to 350 mm in an industrial setting. Usually, the screen roll 52 will be rotated at about 6 to 100 rpm to provide a tangential surface velocity of about 1798 to 30,175 mm/sec.

If desired, both the screen roll 52 and the backing roll 54 may be driven by an external motive force (not shown), or one roll may be driven by external motive force and the second roll driven by frictional engagement with the first roll. An alternating current electric motor having an output of about 1,500 watts has been found to provide adequate motive force. By rotating, the rolls 52 and 54 actuate a depositing means for depositing heated, thermally sensitive material onto the substrate 18 to form the fibers.

The depositing means should be able to accommodate the temperature of the thermally sensitive material in the liquid state, provide substantially uniform pitch in both the machine and cross-machine directions, and yield the desired density of fibers 10 within the array. Also, the depositing means is preferably adjustable to produce fibers having various diameters of the base and heights of the shank. The screen roll 52, specifically, provides for the depositing means to deposit the fibers on the substrate 18 in the desired array, discussed above, (or other pattern) according to the present manufacturing process.

One suitable depositing means for depositing fiber material onto the substrate 18 is the print screen 56 of a screen roll 52. For the embodiment described herein, a screen roll 52 having a mesh which produces about 2.0 to about 8.0 fibers per linear millimeter is useful. A screen roll 52 having a mesh which produces from about 4 fibers to about 7 fibers per millimeter is preferred and a screen roll having mesh which produces about 6 fibers per millimeter is most preferred.

The screen roll 52 and backing roll 54 should be compressed, coincident with the plane connecting the centerlines of the rolls 52 and 54, to press the adhesive from the cells 56 in the print roll onto the substrate 18 and to provide sufficient frictional engagement to drive the opposing roll if it is not externally driven. Generally a pressure of about 5.0 to 60.0 p.s.i. is useful. The backing roll 54 should be somewhat softer and more compliant than the screen roll 52 to provide cushioning of the fiber material as it is deposited on the substrate 18 from the screen roll 52. A backing roll 54 having a rubber coating with a Shore A durometer hardness of about 40 to 60 is suitable.

The screen roll 52 temperature is not critical, however, the screen roll 52 should be heated to prevent solidification of the fibers 10 during transfer and deposition on the substrate 18. Generally, a screen roll 52 surface temperature near the source material temperature is desired. A screen roll 52 temperature of about 100° C. has been found to work well.

One will recognize that a chill roll may be necessary if the substrate 18 is adversely affected by the heat transferred from the fiber material. If a chill roll is desired, it may be incorporated into the backing roll 54 using means well known to one skilled in the art. This arrangement is often necessary if a polypropylene, polyethylene or other polyolefinic substrate is used.

The thermally sensitive material used to form the individual fibers 10 must be kept in a supply tank which provides for the proper temperature to apply the fibers to the substrate. Typically, a temperature slightly above the melting point of the material is desired. The material is considered to be at or above the "melting point" if the material is partially or wholly in the liquid state.

If the temperature of the thermally sensitive is too hot, the thermally sensitive material will flow into a small, somewhat semispherically shaped puddle and a fiber will not be drawn. Conversely, if the source temperature is too low, the thermally sensitive material may not transfer from the supply to the means for depositing 52 the material or, subsequently, may not properly transfer from the depositing means 52 to the substrate in the desired array or pattern. Further, it may cause clogging and obstruction of the depositing means. The source of the material should also impart a generally uniform cross-machine direction temperature profile to the material, be in 40 communication with the means for depositing the adhesive material onto the substrate 18 and easily be replenished or restocked as the fiber material becomes depleted.

The supply is externally heated by known means (not shown) to maintain the fiber material in a liquid state and at the proper temperature. The preferred temperature is above the melting point but below that at which a significant loss of viscoelasticity occurs.

As illustrated in FIG. 5, the screen roll 52 of this invention includes a heated pressure bar 60 and a print screen 56. The thermally sensitive material is fed from a storage trough (not shown) into the inlet port 65 of the heated pressure bar 60. Pressure bar 60 is heated to maintain the thermally sensitive material at its melting point.

The heated thermally sensitive material is fed from the pressure bar 60 onto the inside surface of the screen roll 52. The thermally sensitive material is fed through a slot (not shown) in the bottom of the pressure bar 60 to create an uniform distribution of material across the screen roll 52.

Juxtaposed with the inside surface of the screen roll 52 is a doctor blade 62 which controls the amount of thermally sensitive material applied to the print roll 54. The doctor blade 62 and heated pressure bar 60 are held stationary as the screen roll 52 is rotated, allowing the doctor blade 62 to wipe the inside circumference of the roll 52 to force the fiber material through the screen roll 52 onto the substrate 18. This arrangement allows fiber material to be deposited from the screen roll 52 to the substrate 18 in the desired array, according to the geometry of the screen 56 on the circumference of the screen roll 52. As seen in FIG. 5, the doctor blade 62 is preferentially disposed perpendicularly to the inside surface of the screen roll 52.

After depositing fiber material from the screen 56 onto the substrate 18, the rolls 52 and 54 continue rotation, in the directions indicated by the arrows of FIG. 5. This results in a period of relative displacement between the transported substrate 18 and the screen 56 during which period (prior to severing), the fiber material bridges the substrate 18 and screen roll 52. As relative displacement continues, the fiber material is drawn until severing occurs and the fiber 10 is separated from the screen 56 of the screen roll 52. As used herein the term "draw" means to increase in linear dimensions, at least a portion of which increase becomes substantially permanent for the life of the sheet material. The length of the resulting fibers 10 will vary with the application for the sheet material and the nature of the thermally sensitive material.

After being deposited onto the substrate 18, the fibers 10 may be severed from the screen roll 52. If desired, severing may be accomplished as a separate, dedicated step in the process by utilizing a severing means for severing the prongs into the engaging means of the cloth-like sheet. However, depending upon the adjustment of the various parameters, such as the angle between the substrate and the depositing means, the velocity differential, the viscosity of the heated, thermally sensitive material, the cell, etc., a dedicated and separate severing step may not be necessary. Severing may occur naturally as a function of the substrate being transported away from the point of deposition.

If utilized, the severing means 58 should be adjustable to accommodate various sizes of fibers 10 and also provide uniformity throughout the cross-machine direction of the array. The term "severing means" refers to any apparatus or component which longitudinally severs the fiber 10. The severing means 58 should also be clean and should not rust, oxidize or impart corrodents and contaminants to the fibers. A suitable severing means 58 is a wire disposed generally parallel the centerline of the rolls 52 and 54 and spaced from the substrate 18 a distance which is-somewhat greater than the perpendicular distance from the highest elevation of the solidified fiber to the substrate 18.

Preferably, the wire 58 is electrically heated to prevent build-up of the molten fiber material on the severing means 58 and to accommodate any cooling of the fibers 10 which occurs between the time the fiber material leaves the heated source. The heating of the severing means 58 should also provide for uniform temperature distribution in the cross-machine direction, so that an array of fibers 10 having substantially uniform geometry is produced.

Generally, as the fiber material temperature increases, a relatively cooler hot wire temperature severing means 58 can be accommodated. Also, as the speed of the substrate 18 is decreased, less frequent cooling of the hot wire 58 occurs as each fiber is severed, making a relatively lower wattage hot wire more feasible at the same temperatures. It should be recognized that as the temperature of the hot wire is increased a fiber 10 having a generally shorter shank length will result. Conversely, the shank length will be increased in inverse proportion as the temperature of the hot wire 58 is decreased. It is not necessary that the severing means 58 actually contact the fiber 10 for severing to occur. The fiber 10 may be severed by the radiant heat emitted from the severing means 58.

For the embodiment described herein a round cross section nickel-chromium wire, having a diameter of about 0.51 mm (0.02 inches) heated to a temperature of about 343° C. to about 416° C. has been found suitable. It will be apparent that a knife, laser cutting or other severing means 58 may be substituted for the hot wire 58 described above.

It is important that the severing means 58 be disposed at a position which allows stretching of the fiber material to occur prior to the fiber 10 being severed. If the severing means 58 is disposed too far from the plane of the substrate 18, the fiber material will pass underneath the severing means and not be intercepted by it, forming a very long fiber 10 which will not be properly spaced from the substrate or adjacent fibers. Conversely, if the severing means 58 is disposed too close to the plane of the substrate 18, the severing means 58 will truncate the shank 14 forming an abrasive stump.

A hot wire severing means 58 disposed approximately 12.6 mm to 38.0 mm (½ to 1½ inches), preferably about 9.5 mm (⅜ inches) in the machine direction from the nip point, approximately 5.0 mm to 9.5 mm (0.197 to 0.374 inches) radially outward from the backing roll 54 and approximately 2.0 mm to approximately 7.0 mm (0.079 to 0.275 inches) radially outwardly from the screen roll 52 is adequately positioned for the process of manufacture disclosed herein.

It may also be necessary to sever the individual fibers from the screen roll 52 as part of the process which forms the cloth-like sheet. When severed, a fiber 10 is longitudinally divided into two parts, a base 12 and a distal end 16 which remain with the cloth-like sheet and a moil (not shown) which remains with the screen roll 52 and may be recycled, as desired. After the fibers 10 are severed from the moil, the fibers 10 are allowed to solidify prior to contact of the fibers with other objects. After solidification of the fibers 10, the substrate 18 may be wound into a roll for storage as desired.

The substrate 18 may be transported through the nip 50 in the machine direction at about 3 to about 31 meters per minute (10 to 100 feet per minute). The substrate 18 is preferably drawn through the nip at a speed equal to the tangential speed of the screen roll 52, producing little to no velocity differential. However, with this invention, a velocity differential ±2% will acceptably produce the fibers of this invention. As the velocity differential decreases, the fiber 10 obtains an orthogonal position in relation to the substrate 18. For that reason, the substrate 18 and the screen roll 52 preferably have no velocity differential and move at a 1:1 ratio.

One skilled in the art should consider the radius of curvature of the screen roll 52 and its relationship to the velocity differential and the angle between the substrate 18 and the plane of the nip 50. As the radius of the curvature of the screen roll 52 decreases, the moil and shank 14 of the fiber 10 being formed are drawn away from the substrate 18 at an angle which, in the vicinity of the nip 50 is more orthogonal the plane of the nip. Upon solidification, such a fiber 10 will typically be relatively straighter than a fiber 10 manufactured under conditions which are similar, except for the use of a larger radius of curvature screen roll 52. Thus, to provide an improved sheet according to the present invention, it is important to provide with the apparatus used to manufacture the sheet a means for imparting a vector orientation which is near orthogonal (no more than about 10° off axis in any direction) the plane of the substrate 18 at the base 12 of the fiber 10 to the discrete amounts of deposited, thermally sensitive material.

Once the thermally sensitive material has been deposited onto the substrate 18 and severed, the sheet can then be subjected to a bonding process to form a nonwoven matrix as described above. This process includes thermal discrete point bonding, pressure, ultrasonic or other well-known fiber bonding techniques. The sheet material, whether bonded or unbonded, may then be used to form a top sheet, core wrap, backsheet or cuff for a disposable absorbent article.

Although it is preferred that the fibers 10 are not connected in any direction, the fibers 10 may be interconnected laterally in the machine direction. To achieve this interconnection, the source of the thermally sensitive material is heated to a temperature which exceeds the melting point of the material and causes a reduction in the viscosity of the material. The material becomes "runny" and, as it is applied, the distal end 16 of one fiber will become laterally connected in the machine direction to the fiber 10 in the next row.

Although this disclosure describes a substrate 18 which has a thermally sensitive material coated on one side, those skilled in the art will recognize that the same process can be used to provide substrate 18 which is coated on both sides with a thermally sensitive material.

Several variations of the disclosed apparatus and method are feasible and within the scope of the claimed invention. If desired, by providing a relatively strong substrate and sufficient tension, the backing roll 54 of the apparatus of FIG. 5 may be omitted. Instead, as is well known to one skilled in the art, the substrate 18 may wrap the print roll by the use of tracking rolls which produce an S-shaped arc about the printing roll. In this configuration, there is no nip 50 as disclosed in FIG. 5, but, rather, the tension of the substrate provides for deposition of the heated, thermally sensitive material from the cells of the screen roll 52. However, one should recognize that if this variant configuration is selected for the apparatus and means for depositing the heated, thermally sensitive material onto the substrate 18, the substrate 18 must have sufficient tensile strength to avoid tearing and to maintain the tension necessary for proper deposition of the heated thermally sensitive material.

EXAMPLES

Provided below are illustrative nonlimiting examples of the various fibers produced by the method of this invention.

Example 1

Figure 1:
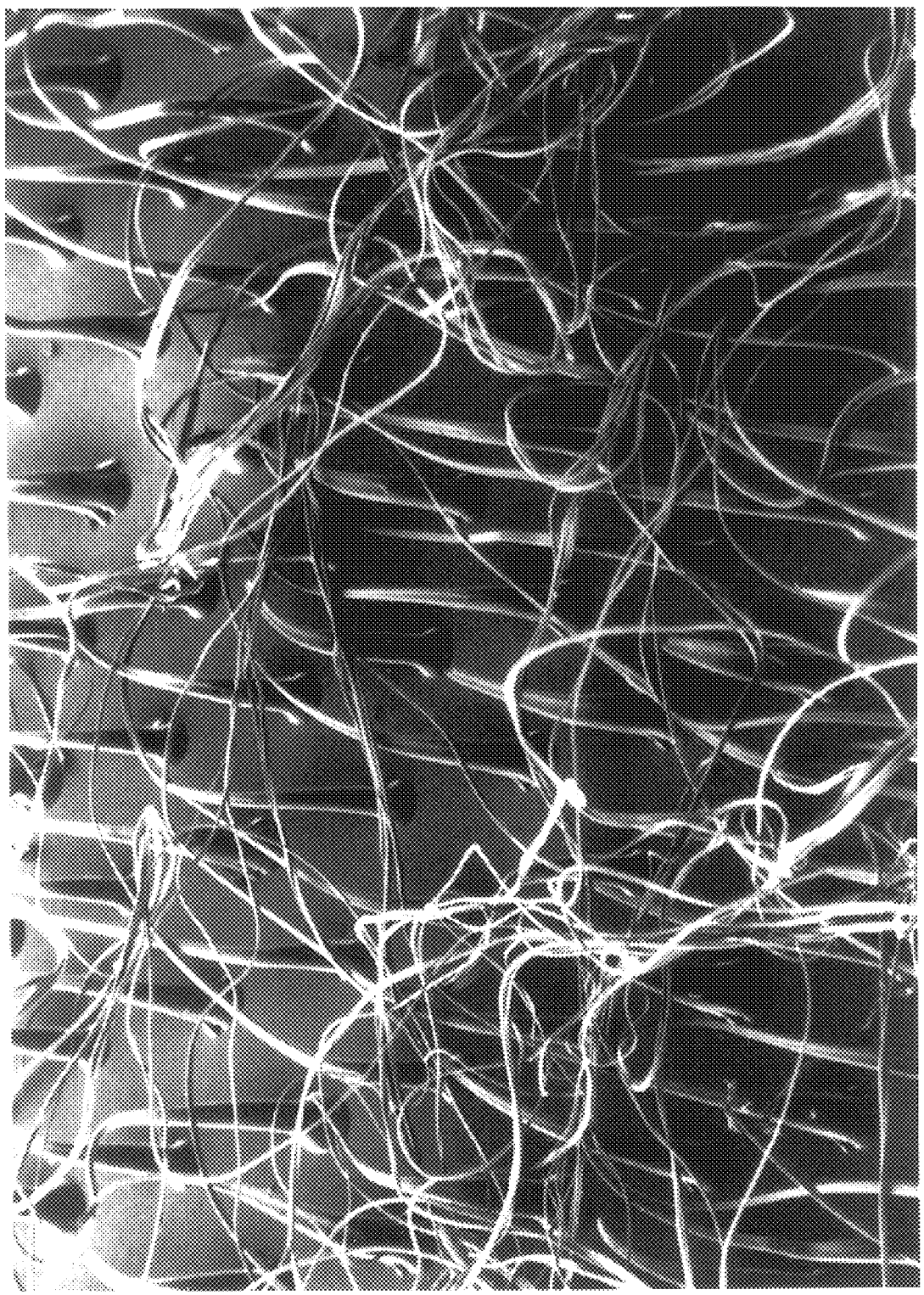
FIG. 1 is a scanning electron microgram showing a long, unbonded fiber mat of this invention.
Figure 2:
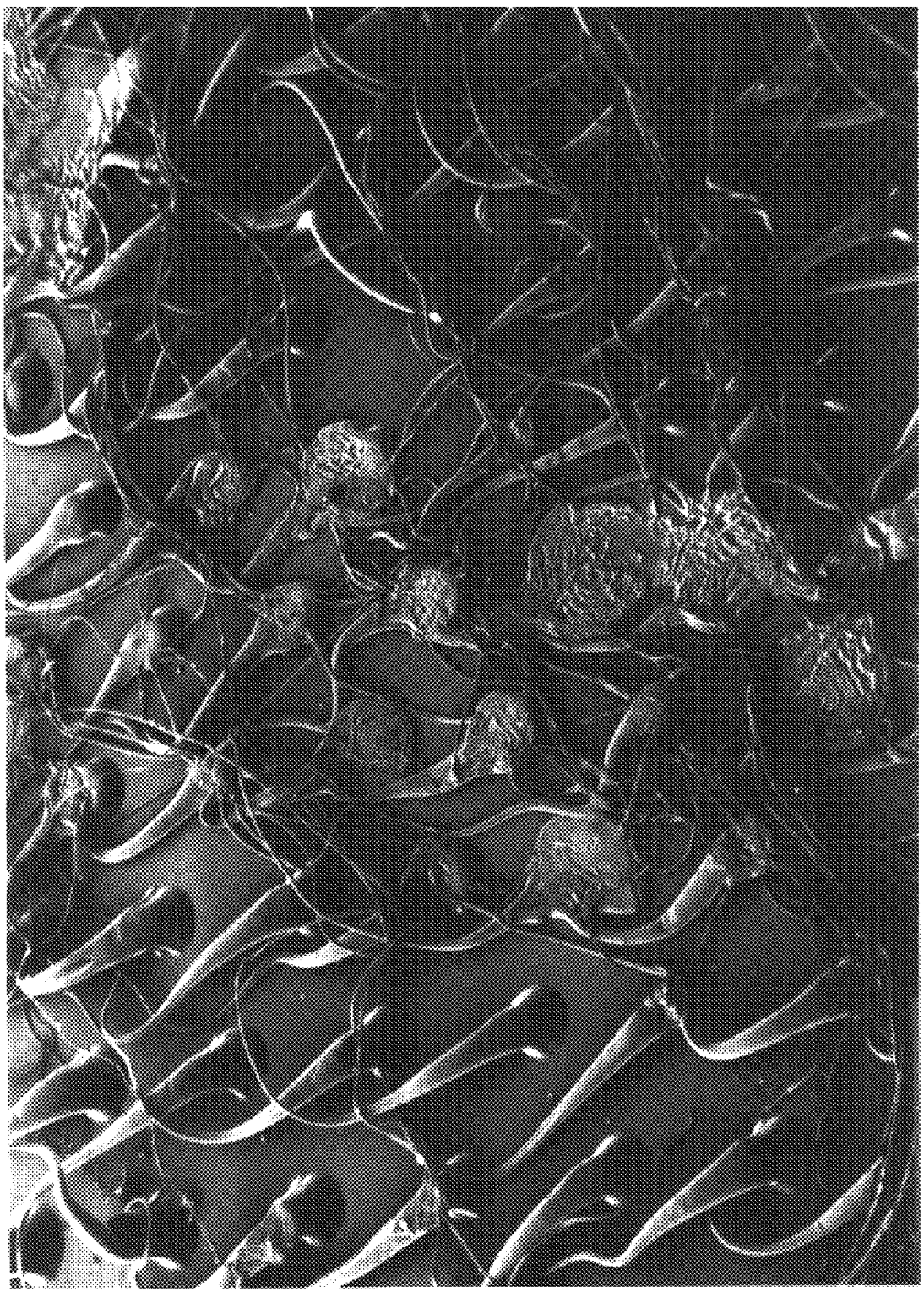
FIG. 2 is a scanning electron microgram showing a long, thermally bonded fiber mat of this invention.
Figure 3:
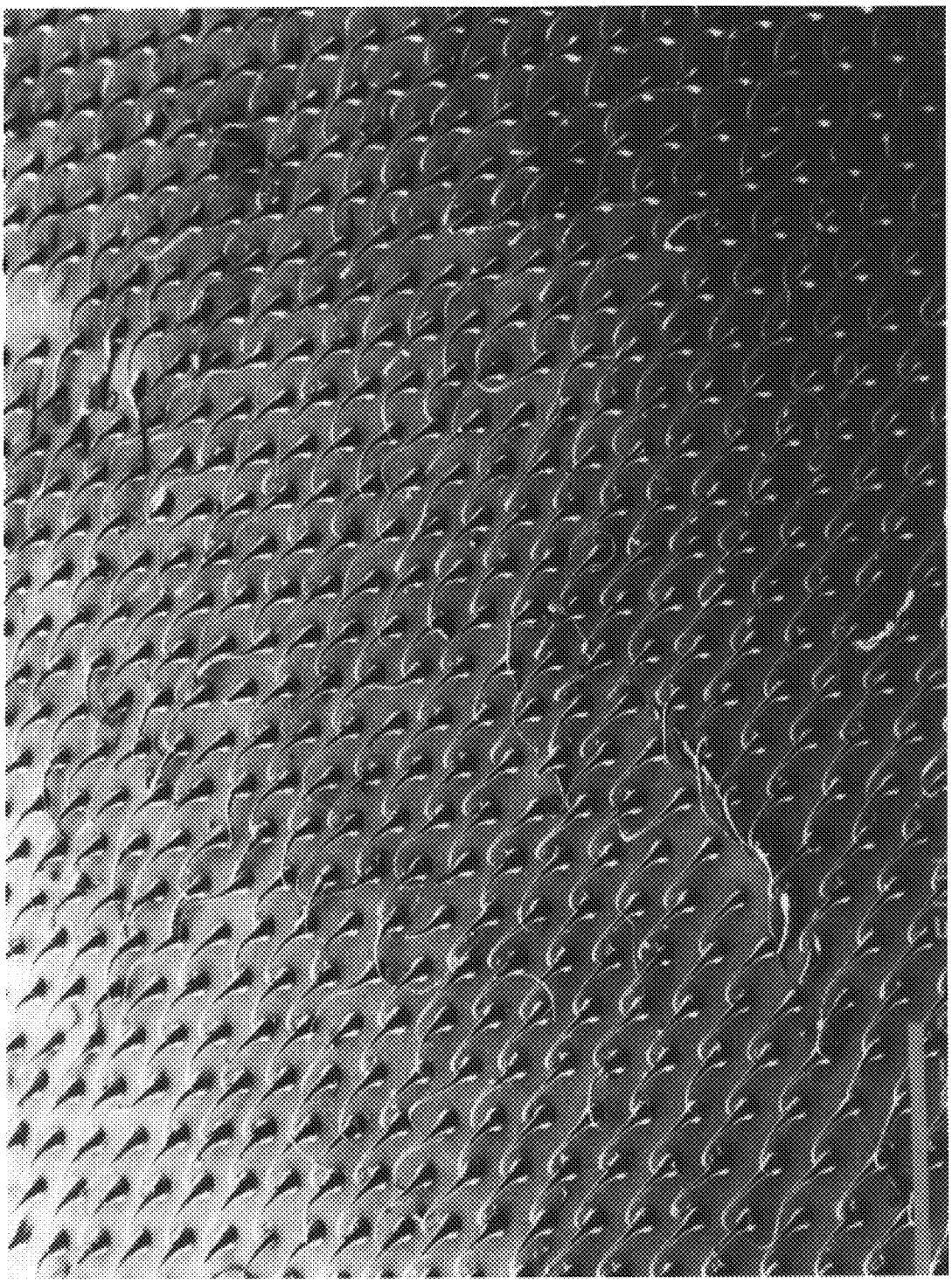
FIG. 3 is a scanning electron microgram showing a short, unbonded fiber mat of this invention.

Referring to FIG. 3, the fibrous sheet produced by the method of this invention has a pitch of 6.1 fibers per mm resulting in a fiber density of 37.2 fibers per $mm^2$ Each fiber has a base of approximately 0.04 mm and fiber denier ranging from 0.2 to 0.3. The fibers produced range in length approximately from 0.15 to 0.40 mm. The materials used were a cast film as the substrate and a low density polyethylene-type resin for the fibers. Such a material would be useful for applications in absorbent articles where a fluid barrier is desirable, such as the backsheet or cuffs of a disposable absorbent garment.

Example 2

A fibrous sheet produced by the method of this invention having a pitch of 6.1 fibers per mm also resulting in a fiber density of 37.2 fibers per $mm^2$. Each fiber having a base of approximately 0.04 mm and a fiber denier ranging from 0.2 to 0.3. The fibers produced range in length approximately from 0.15 to 0.40 mm. The substrate being a perforated film sheet and the fibers made using any suitable thermoplastic olefinic resin, such as low density polyethylene. Such a material would be used in absorbent articles where fluid permeability is desirable, such as a topsheet or a tissue.

It will be apparent to one skilled in the art that various other modifications and combinations of the parameters described above may be utilized. For example, multiple parameters may be adjusted, including different hot wire temperatures, different hot wire positions, other velocity differentials, and different means for depositing the heated, thermally sensitive material onto the transported substrate are feasible. All such combinations and permutations are within the scope of the following claims.

What is claimed is:

1. A sheet material having at least one fibrous surface exhibiting the appearance and texture similar to a fibrous cloth comprising:

a substrate; and an array of free formed fibers wherein each fiber is drawn from a discrete deposit of a thermally sensitive material joined to at least one surface of said substrate, said substrate serving as a fiber base, said fiber having an essentially straight shank extending outwardly from the base to a distal end, said array of fibers having a density of about 4 to 62 fibers per square millimeter.

2. The sheet material of claim 1 wherein said array of essentially straight fibers has a density of about 16 fibers per square millimeter to about 49 fibers per square millimeter.

3. The sheet material of claim 2 wherein said array of fibers has a density of about 37 fiber bases per square millimeter.

4. The sheet material of claim 1 wherein said essentially straight fibers are ethylene/vinyl acetate fibers or polyethylene fibers.

5. The sheet material of claim 1 wherein said essentially straight fibers are about 0.15 to 65 mm long.

6. The sheet material of claim 1 wherein said essentially straight fibers have a denier of about 0.20 to 6.0.

7. The sheet material of claim 1 wherein said sheet exhibits a shear strength of less than 50 $g/m^2$.

8. The sheet material of claim 1 wherein said sheet exhibits a peel strength of about 0 $g/in^2$.

9. The sheet material of claim 1 wherein said substrate is selected from the group consisting of a knitted fabric, a woven material, a non-woven material, rubber, vinyl, polyolefinic film, and paper.

10. The sheet material of claim 9 wherein said substrate is a polyethylene film.

11. The sheet material of claim 1 wherein said sheet material is a top sheet, core wrap, backsheet, or cuff for a disposable, absorbent garment.

* * * * *

UNITED STATES PATENT AND TRADEMARK OFFICE
CERTIFICATE OF CORRECTION

PATENT NO. : 6,136,405
DATED : October 24, 2000
INVENTOR(S) : Terrill Alan Young et al.

It is certified that error appears in the above-identified patent and that said Letters Patent is hereby corrected as shown below:

<u>Column 2,</u>
Line 19, delete "4,058,247" and insert therefor -- 5,058,247 --.

Signed and Sealed this

Twentieth Day of November, 2001

Attest:

*Nicholas P. Godici*

NICHOLAS P. GODICI
*Attesting Officer*     *Acting Director of the United States Patent and Trademark Office*